United States Patent
Bojrab

(10) Patent No.: US 9,504,501 B2
(45) Date of Patent: Nov. 29, 2016

(54) SYSTEMS AND METHODS FOR REDUCING PRESSURE WITHIN A SPINAL DISC

(71) Applicant: Louis Bojrab, Northville, MI (US)

(72) Inventor: Louis Bojrab, Northville, MI (US)

(*) Notice: Subject to any disclaimer, the term of this patent is extended or adjusted under 35 U.S.C. 154(b) by 0 days.

(21) Appl. No.: 14/867,671

(22) Filed: Sep. 28, 2015

(65) Prior Publication Data

US 2016/0015431 A1  Jan. 21, 2016

Related U.S. Application Data

(62) Division of application No. 13/713,277, filed on Dec. 13, 2012, now abandoned.

(51) Int. Cl.
| | |
|---|---|
| *A61B 17/70* | (2006.01) |
| *A61F 2/44* | (2006.01) |
| *A61F 2/86* | (2013.01) |
| *A61F 2/95* | (2013.01) |
| *A61B 17/00* | (2006.01) |
| *A61B 17/56* | (2006.01) |

(52) U.S. Cl.
CPC ....... *A61B 17/7061* (2013.01); *A61B 17/0057* (2013.01); *A61B 17/00234* (2013.01); *A61F 2/442* (2013.01); *A61F 2/86* (2013.01); *A61F 2/95* (2013.01); *A61B 2017/00004* (2013.01); *A61B 2017/561* (2013.01); *A61B 2017/564* (2013.01); *A61F 2002/4435* (2013.01); *A61F 2002/4475* (2013.01)

(58) Field of Classification Search
CPC .................. A61F 2002/4435; A61F 2002/444
USPC .............................. 623/17.11–17.16; 606/279
See application file for complete search history.

(56) References Cited

U.S. PATENT DOCUMENTS

| | | |
|---|---|---|
| 2003/0074075 A1 | 4/2003 | Thomas, Jr. et al. |
| 2003/0158604 A1* | 8/2003 | Cauthen, III ........... A61F 2/441 623/17.16 |
| 2005/0278027 A1 | 12/2005 | Hyde, Jr. |
| 2006/0100706 A1 | 5/2006 | Shadduck et al. |
| 2006/0247785 A1 | 11/2006 | Gorensek et al. |
| 2006/0253132 A1 | 11/2006 | Evans et al. |
| 2007/0093899 A1 | 4/2007 | Dutoit et al. |
| 2007/0093905 A1 | 4/2007 | O'Neil et al. |
| 2007/0100348 A1 | 5/2007 | Cauthen, III et al. |
| 2008/0262628 A1 | 10/2008 | Laitenberger et al. |
| 2009/0112321 A1 | 4/2009 | Kitchen |
| 2010/0049003 A1 | 2/2010 | Levy |
| 2010/0286782 A1 | 11/2010 | Schaller et al. |

* cited by examiner

*Primary Examiner* — Pedro Philogene
*Assistant Examiner* — David C Comstock
(74) *Attorney, Agent, or Firm* — Stamoulis & Weinblatt LLC

(57) ABSTRACT

Systems and methods for reducing pressure within a spinal disc are described. In accordance with one implementation, a spinal disc system comprises an aperture within a spinal disc body, and the aperture is configured to permit nucleus pulposus to flow from the disc body through the aperture. In accordance with another implementation, a method of reducing pressure within a spinal disc comprises forming an aperture within a spinal disc body, and permitting at least a portion of the nucleus pulposus to flow from the disc body through the aperture.

21 Claims, 6 Drawing Sheets

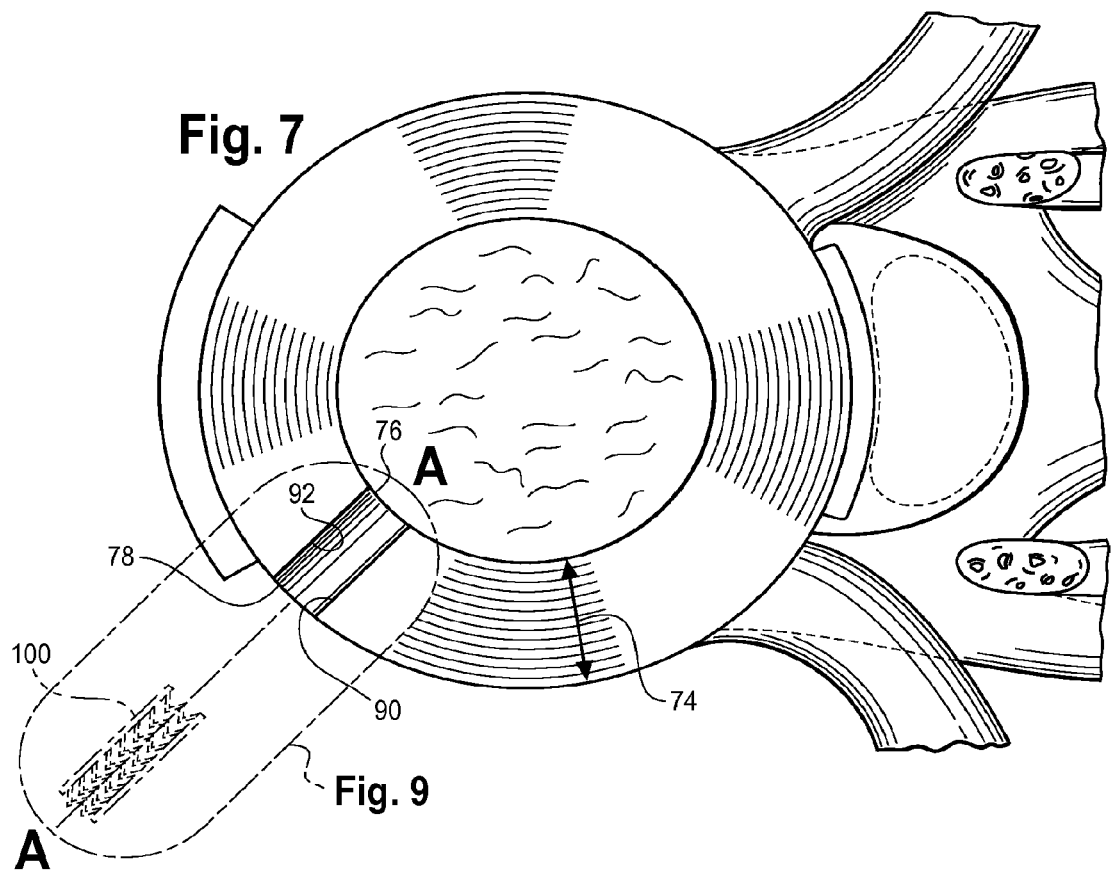
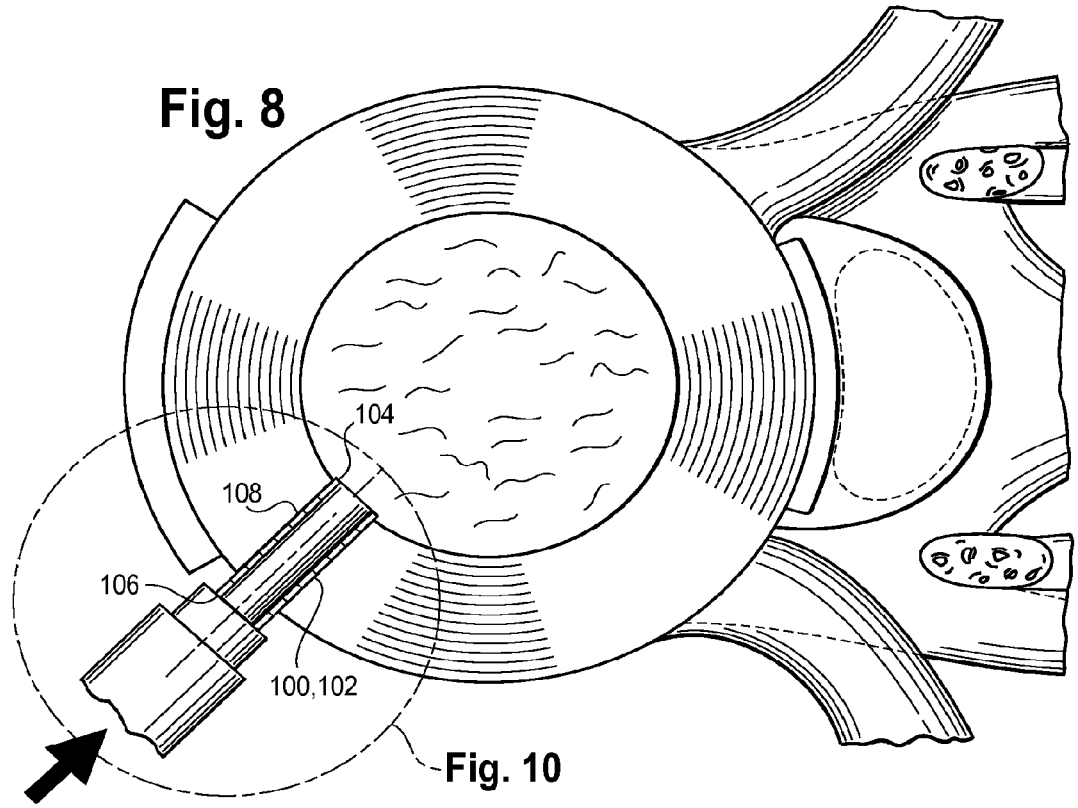

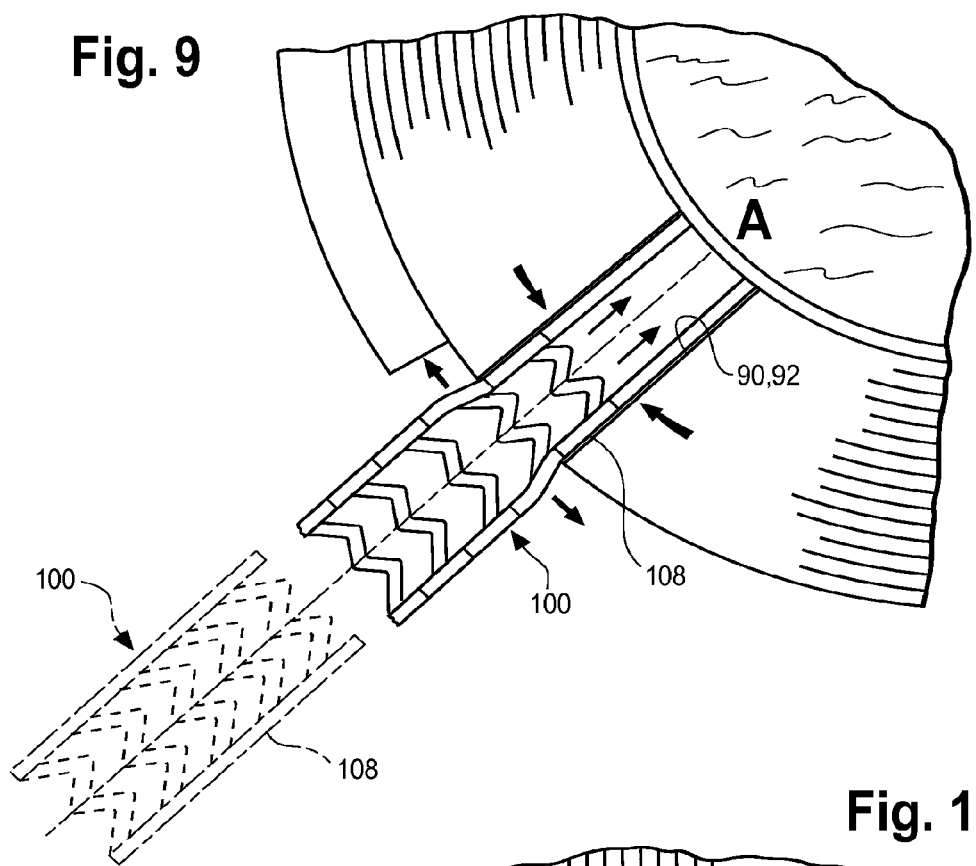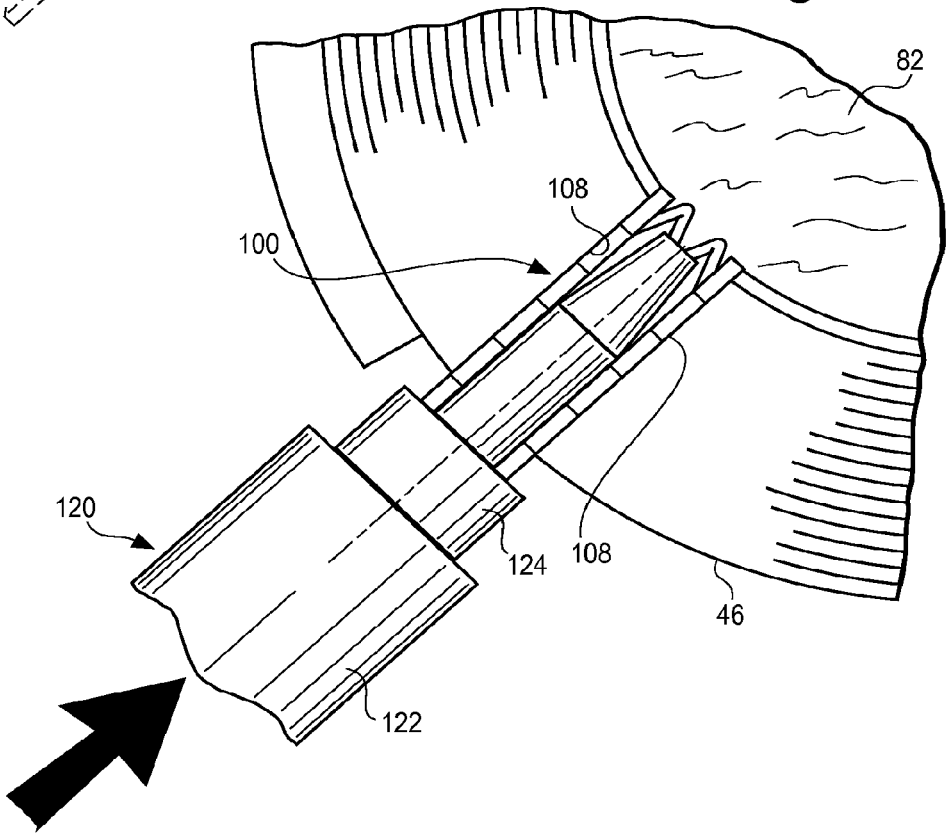

SYSTEMS AND METHODS FOR REDUCING PRESSURE WITHIN A SPINAL DISC

This application claims priority to and is a divisional application of U.S. Ser. No. 13/713,277 entitled "SYSTEMS AND METHODS FOR REDUCING PRESSURE IN A SPINAL DISC," which disclosure is incorporated herein in its entirety.

TECHNICAL FIELD

This application relates generally to spinal disc systems and methods for reducing pressure within a spinal disc.

BACKGROUND

A human spinal column includes vertebral bodies alternating with intravertebral discs extending from the neck to the pelvis. The discs generally form strong joints, separate, cushion and allow flexure and torsion between the vertebrae.

When functioning properly, the vertebrae and discs allow a person to bend forward, backward, sideways and to twist. To accomplish this, the discs typically permit adjacent vertebrae six degrees of motion: vertical (compressing to absorb shock and tension), bending forward and backward, bending to the sides and twisting. The cervical and lumbar discs also can be thicker anteriorly to contribute to lordosis. Thoracic discs usually are more uniform. Unfortunately, disc disease may limit spinal motion or cushioning or permit the motion with pain.

Each intervertebral disc usually has a central area composed of a colloidal gel, called the nucleus pulposus, on a surrounding collagen-fiber composite structure, the annulus fibrosus. The nucleus pulposus typically occupies 25-40% of the disc's total cross-sectional area. The nucleus pulposus usually contains 70-90% water by weight and may mechanically function like an incompressible hydrostatic material. The annulus fibrosis surrounds the nucleus pulposus and typically resists torsional and bending forces applied to the disc. The annulus fibrosis thus often serves as the disc's main stabilizing structure. The annulus fibrosus usually resists hoop stresses due to compressive loads and the bending and torsional stresses produced by a person bending and twisting. The fibers of the annulus form lamellae, individual layers of parallel collagen fibers, that attach to the superior and inferior end plates of adjacent vertebrae. Vertebral end-plates separate the disc from the vertebral bodies on either side of the disc.

The anterior longitudinal ligament, which is anterior to the vertebral bodies, and the posterior longitudinal ligament, which is posterior to the vertebral bodies and anterior to the spinal cord function to hold the spinal structure together. The muscles of the trunk provide additional support.

Trauma or disease may displace or damage spinal discs. A disc herniation occurs when annulus fibers weaken, and the inner tissue of the nucleus (nucleus pulposus) bulges out of the annulus. The herniated nucleus may compress a spinal nerve, which could result in pain, lack of sensation, loss of muscle control or even paralysis. Alternatively, disc degeneration may result when the nucleus deflates. Subsequently, the height of the nucleus decreases often causing the annulus to buckle in areas where the laminated plies are loosely bonded. This also may cause chronic and severe back pain. Further, the disc may rupture, resulting in a portion of the nucleus pulposus flowing through the fractured annulus, outside the disc to compress nerves and/or the spinal cord. This material may irritate the spinal nerve or spinal cord when tit flows into a posterior region of the disc.

Whenever the nuclear tissue is herniated or the disc degenerates, the vertical disc space typically narrows and the adjacent vertebra may lose much of their normal stability. In many cases, to alleviate pain from degenerated or herniated discs, a surgeon removes the nucleus by performing a discectomy, which requires surgical dissection. The healing from such a surgery usually causes scar tissue which may compress the same or nearby nerves and/or spinal cord (which were being affected by the now-removed nucleus) and cause chronic pain and nervous system dysfunction. Other times, if the disc is compressed, the surgeon may perform a surgical fusion of two or multiple adjacent vertebrae together. While this treatment may or may not alleviate the pain and nervous dysfunction, the patient often loses all disc motion in the fused segment. Ultimately, this procedure places greater stress on the discs adjacent to the fused segment as the adjacent discs compensate for lack of motion.

In the case of severe disc degeneration, the height of the disc often is flattened to such an extent that the adjacent vertebral body bones touch and eventually grow together. This may stop pain by stopping the movement of the disc between the vertebral bones, and is known as an auto-fusion.

SUMMARY

In accordance with one implementation, a spinal disc system comprises an aperture within a spinal disc body, and the aperture is configured to permit nucleus pulposus to flow from the disc body through the aperture.

In accordance with another implementation, a method of reducing pressure within a spinal disc comprises forming an aperture within a spinal disc body, and permitting at least a portion of the nucleus pulposus to flow from the disc body through the aperture.

BRIEF DESCRIPTION OF THE DRAWINGS

In the drawings, which are discussed below, one or more implementations are illustrated. The drawings are not necessarily to scale and certain features may be removed, exaggerated, moved, or partially sectioned for clearer illustration. It is understood that the spinal disc stent is not limited to the implementations depicted in the drawings herein, but rather it is defined by the claims appended hereto and equivalent structures.

FIG. 7 is the view of FIG. 4, illustrating an aperture formed within the wall of a disc, and showing an optional stent, according to an implementation.

FIG. 8 is the view of FIG. 4, illustrating a cannula for implanting a stent within the wall of a disc, according to an implementation.

FIG. 9 is an enlarged sectional view of FIG. 8, illustrating the stent of FIG. 2, according to an implementation.

FIG. 10 is an enlarged sectional view taken of FIG. 8.

Like reference symbols in the various drawings indicate like elements.

DETAILED DESCRIPTION

While the specification concludes with claims particularly pointing out and distinctly claiming subject matter, the spinal disc stent will now be further described by reference to the following detailed description of exemplary implementations taken in conjunction with the above-described accompanying drawings. The following description is presented to enable any person skilled in the art to make and use the spinal disc stent. Descriptions of specific implementations and applications are provided only as non-limiting examples and various modifications will be readily apparent to those skilled in the art. The general principles defined herein may be applied to other implementations and applications without departing from the spirit and scope of the spinal disc stent. Thus, the spinal disc stent is to be accorded the widest scope encompassing numerous alternatives, modifications, and equivalents consistent with the principles and features disclosed herein. For purpose of clarity, details relating to technical material that is known in the technical fields related to the spinal disc stent have not been described in detail so as not to unnecessarily obscure the present application.

Figure 1:
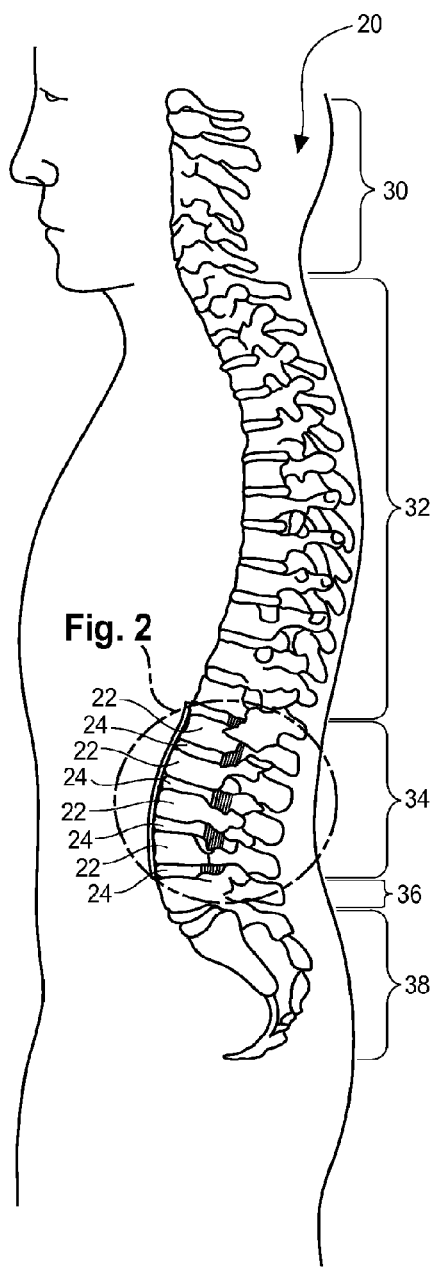
FIG. 1 is side view of a human spinal column.

FIG. 1 illustrates a human spinal column 20. The spinal column 20 includes vertebral bodies 22 alternating with intravertebral discs 24 extending from the neck region to the pelvis (not shown). The vertebral bodies 22 typically include seven cervical vertebrae 30 in the neck, 12 thoracic vertebrae 32 below the neck, five lumbar vertebrae 34 of the lower back, one sacrum 36 below the lumbar region and one coccyx 38.

Figure 2:
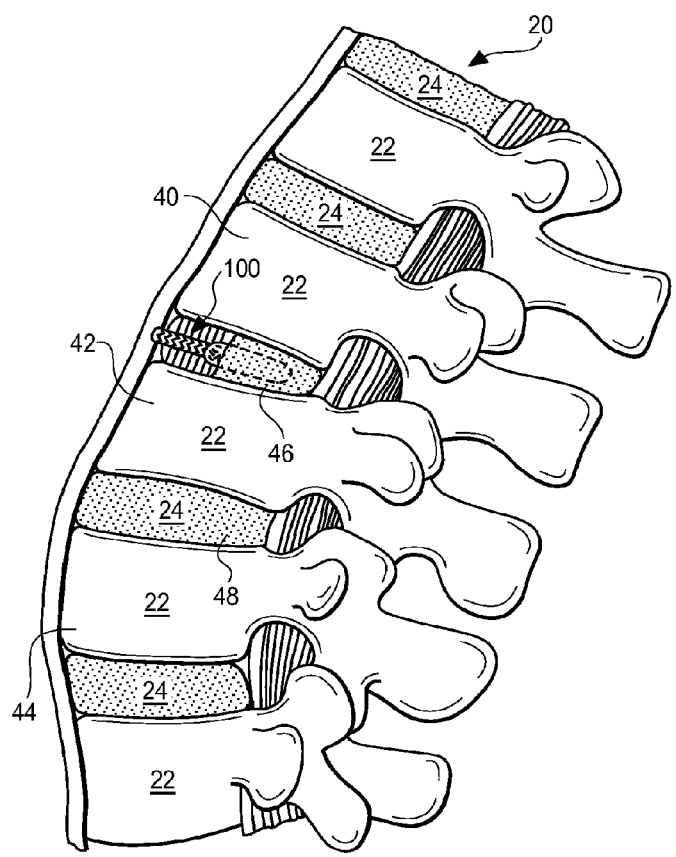
FIG. 2 is an enlarged view of a portion of the column of FIG. 1, illustrating vertebrae alternating with vertebral discs and a stent implanted within the wall of one disc.
Figure 3:
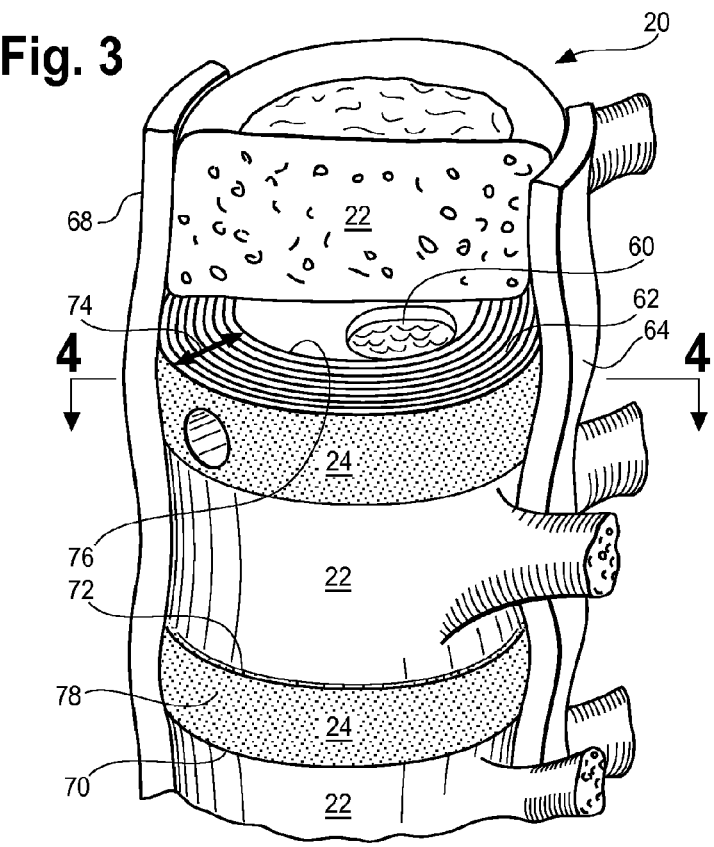
FIG. 3 is a perspective, partially sectioned view of FIG. 2, taken generally along the view of line 3-3 of FIG. 2, with the stent removed for clarity.
Figure 4:
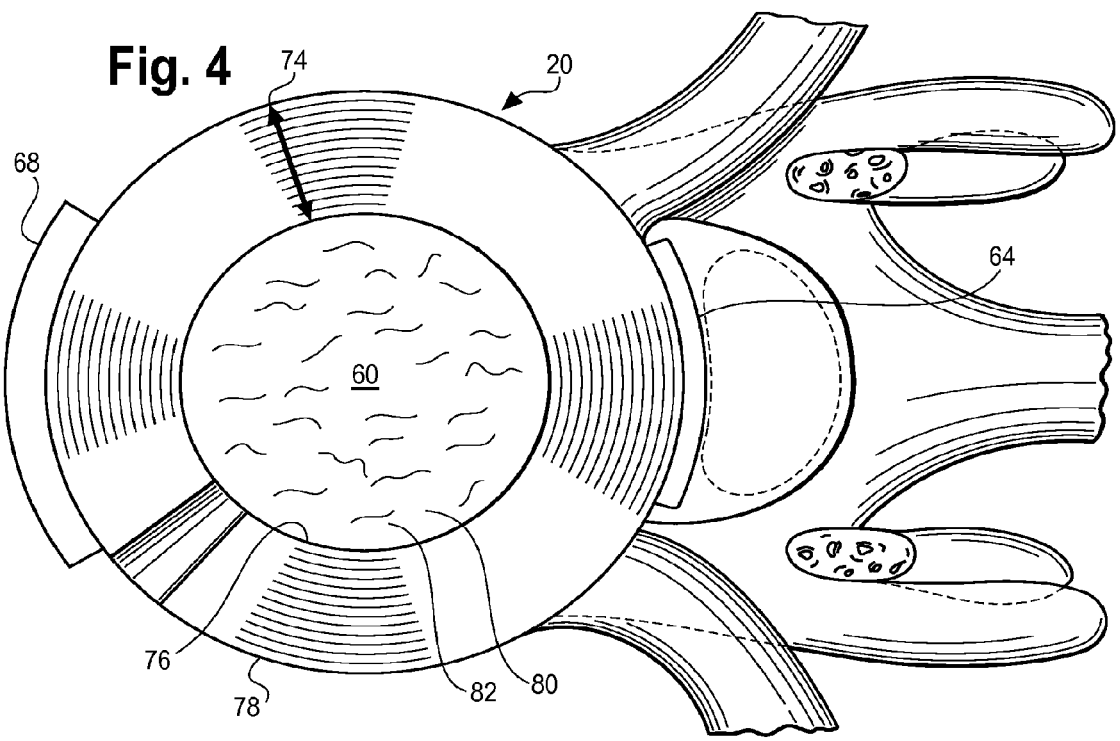
FIG. 4 is a sectional view taken generally along line 4-4 of FIG. 3.

FIGS. 2-8 illustrate a portion of the vertebral bodies 22 as adjacent vertebral bodies 40, 42 and 44 with alternating discs 46 and 48, which are a portion of the discs 24. As seen in FIGS. 3-8, each disc 24 has a nucleus pulposus 60 surrounded by a disc body, or annulus fibrosus, 62. As seen in FIG. 4, the column 20 also includes posterior longitudinal ligaments 64 and anterior longitudinal ligaments 68, which generally maintain the positions of the vertebral bodies 22 relative to discs 24. Other ligaments, which are not discussed, are also typically present. The disc body 62 includes a generally circular lower portion 70, a generally circular upper portion 72, and a generally annular disc wall 74 (FIG. 4). The disc wall, as illustrated in FIGS. 3, 7 and 8, is composed of fibrous tissue, or annulus fibrosus, and includes an inner surface 76 and an outer surface 78. The disc 24 inner surface 76 defines a chamber 80 where the nucleus pulposus 60 is positioned. Further, the disc 24 includes a disc annulus central portion 82 which includes at least a portion of the chamber 80.

As seen in FIG. 2, the spinal column 20 includes a posterior region and an anterior region. In an implementation, a stent 100 may permit the nucleus pulposus 60 to flow into the anterior region of the column 20. In some implementations, a stent is not needed and the nucleus pulposus 60 may flow into the anterior region of the column 20 through the aperture.

FIG. 7 illustrates an aperture 90 formed through the annular disc wall 74 from the inner surface 76 to the outer surface 78. The aperture 90 is generally defined by an inner surface 92. In some implementations, the aperture 90 may be created by a stent, burn hole, drill hole, incision or puncture with balloon dilation or any other suitable manner of forming the aperture 90.

FIGS. 2 and 8 also illustrate an implementation of a disc stent 100. As shown, the stent 100 includes a helical body 102 generally defining an axis A-A and having a first end 104, a second end 106, and an outer surface 108 (FIGS. 9 and 10). In the implementation illustrated, the stent 100 is a biocompatible material, as discussed in greater detail below.

Figure 5:
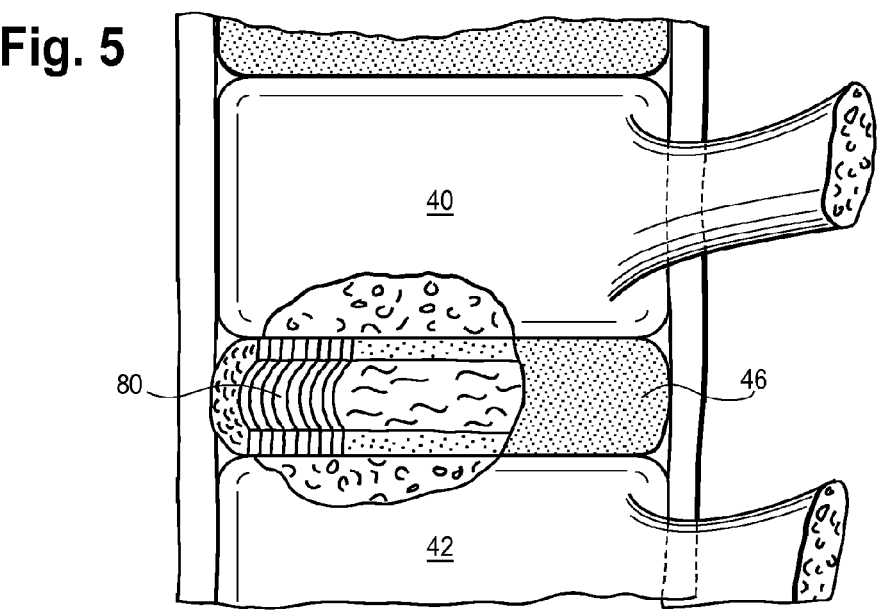
FIG. 5 is a partially sectioned side view of selected vertebrae and a disc of FIG. 2, illustrating the disc in a first configuration.
Figure 6:
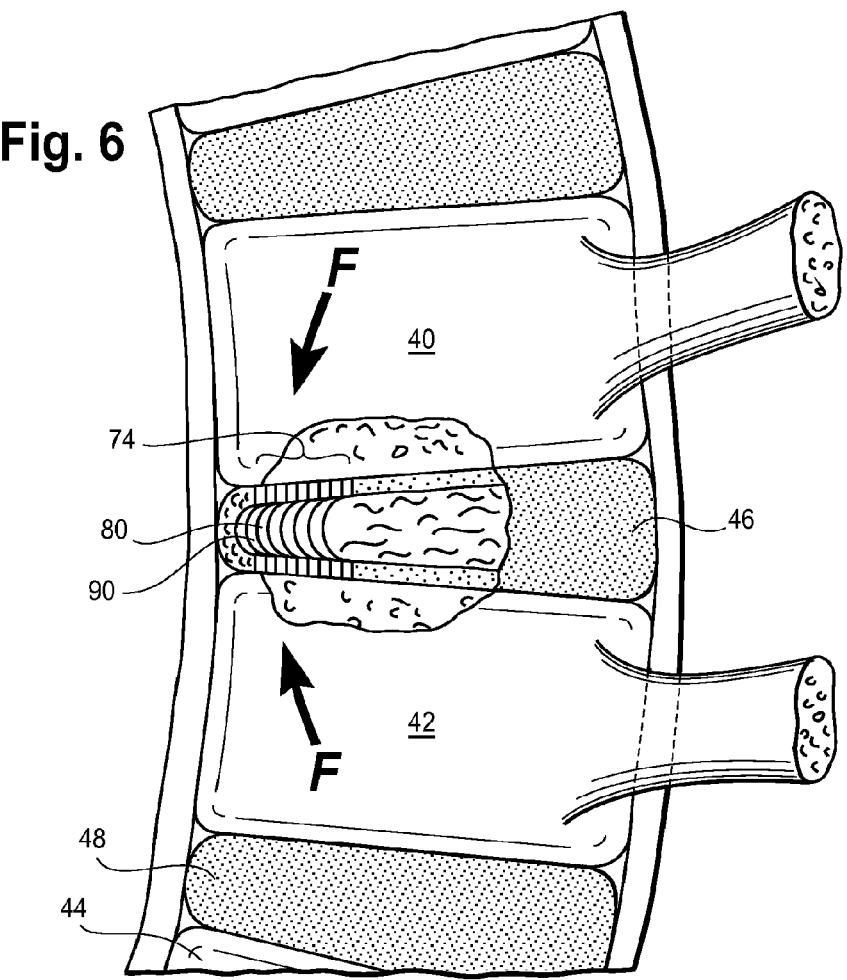
FIG. 6 is a partially sectioned side view of selected vertebrae and a disc of FIG. 2, illustrating the disc in a second configuration.

FIGS. 5 and 6 illustrate relative axial motion between vertebral bodies 40, 42 and the deflection of the disc 24. In FIGS. 5 and 6, the sectional shape of the inside surface 76 of the chamber 80 is exaggerated for clarity of illustration. In FIG. 5, the disk 40 is at a "normal" position relative to the disc 42 and the chamber 80 is illustrated as being generally circular in section. In FIG. 6, the disc 40 is forced toward the disc 42 with a force F as the disc 46 is deformed and the chamber 80 is distorted toward a more ellipsoidal section. As the disc 46 deforms, the disc wall 74 and the aperture 90 may also distort. Accordingly, the stent 100 may need to be radially flexible in order to maintain an axial position within the disc wall 74. Further, in an implementation, a coating 110 may be applied to the outer surface 108 of the stent 100 to promote adhesion between the stent 100 and the inner surface 92 of the aperture 90 to restrict axial motion (along the axis A-A of FIG. 9) of the stent 100 relative to the aperture 90, thereby desirably retaining the stent 100 within the disc wall 74. In some implementations, the stent 100 may be desired to remain within the aperture 90 for only a few (1-12) weeks, and some relative movement between the stent 100 and the inner surface 92 of the disc aperture 90 may be permitted.

FIG. 9 illustrates the stent 100 interposed at least partially within the aperture 90. As illustrated, after the stent 100 is implanted, the stent 100 will deflect radially outward and the aperture 90 may deflect radially inward until the outer surface 108 of the stent 100 contacts and interferes with the inner surface 92 of the aperture 90. The outer surface 108 of the stent 100 may have a relatively smooth, semi-smooth, rough, or semi-rough surface, as desired, to desirably retain the stent 100 within the aperture 90.

FIG. 10 illustrates a device 120 including a cannula 122 and a plunger 124. In some implementations, the cannula 122 includes a deployment end 130 and an opposing operating end (not shown). To deploy the stent 100 within the aperture 90, the stent 100 is first radially compressed and inserted into the deployment end 130 of the cannula 122. Then the cannula 122 is advanced into the body of the patient and into the disc 46, through the disc annulus central portion 82 and into the aperture 90. The plunger 124 may be then used to maintain the position of the stent 100 relative to the aperture 90 as the cannula 122 is retracted, generally in the direction R of FIG. 10. As the deployment end 130 is retracted past the stent body 102, the stent body 102 may radially deform outwardly as the stent outer surface 108 interferes with the inner surface 92 of the aperture 90.

In the implementation illustrated, the stent 100 is implanted entirely within the aperture 90 such that the entire circumference of at least a portion of the stent 100 is in contact with the disc wall 74. Once the stent 100 is implanted into the aperture 90, an aperture 140 (FIG. 9) is formed which permits at least a portion of the nucleus pulposus 60 to flow through the aperture 140 from the chamber 80 to the anterior or lateral region (FIG. 2).

It may be desired to permit the nucleus pulposus 60 to flow through the aperture 140 from the chamber 80 to the anterior/lateral region for a limited amount of time. Accordingly, in some implementations, the aperture 140 may be desirably restricted. In some implementations, the stent 100 may be removed from the annulus fibrosus 74 and the aperture 90 may be permitted to close. In some implementations, the stent 100 may be collapsed or deformed such that the aperture 140 may restrict the flow of the nucleus pulposus 60. In some implementations, all or substantially all of the nucleus pulposus 60 may be permitted to flow through the aperture 140.

Figure 14:
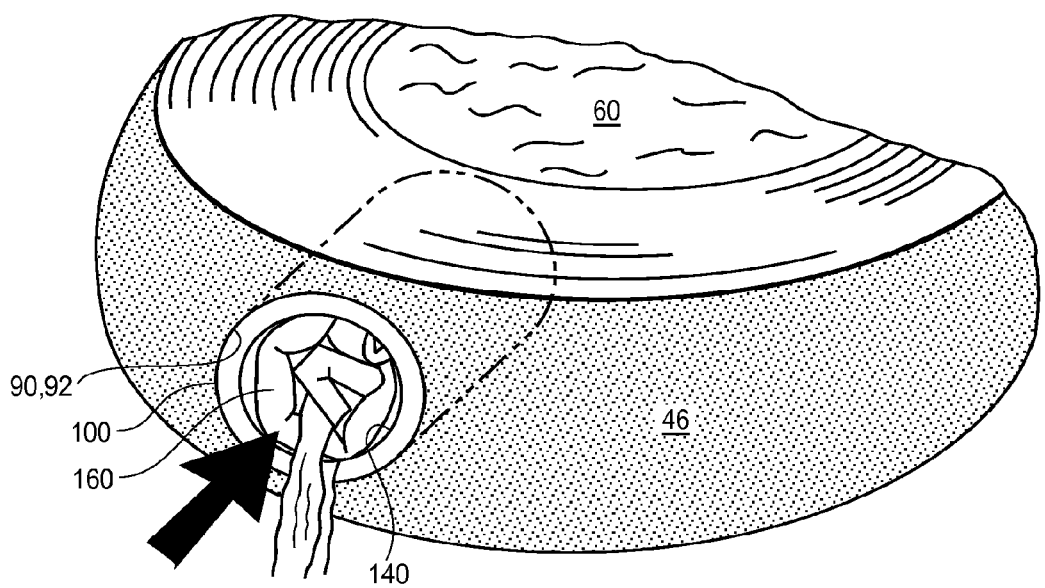
FIG. 14 is a perspective view of a plugging portion, according to an implementation.

In some implementations, the aperture 140 may be restricted by engaging a plugging portion with the stent 100. A non-limiting example of a plugging portion is a threaded portion that is proportioned to threadably engage within a helical stent by rotating the plugging portion as the plugging portion is advanced into the stent 100. Another non-limiting example of a plugging portion is illustrated in FIG. 14, where an elongated biocompatible material 160 is wadded or folded prior to insertion within the aperture 140. In some implementations, the material 160 may desirably embed within the aperture 140 and may restrict the flow of the nucleus pulposus 60. In some implementations, the stent 100 may be constructed of a biodegradable material that will degrade sufficiently within a desirable timeframe that permits the aperture 90 to close, thus restricting the flow of the nucleus pulposus 60. That is, the aperture 90 may heal to restrict the flow of the nucleus pulposus 60. In some implementations, the inner surface 92 of aperture 90 may be treated, such as by heating, freezing, or other suitable method to provide an opening to permit the flow of nucleus pulposus 60 therethrough, where the inner surface 92 treatment will delay the healing of the aperture 90 until about a desired amount of time has been expended.

A non-limiting example of deforming the stent 100 is to melt or fuse the end 106 of the stent 100 with a device that may heat the end 106. Many biocompatible and/or biodegradable materials are constructed of a material such as polyethylene terephthalate (PET) that will deform when subjected to a temperature above the softening point. A device such as a radiofrequency probe, laser or other suitable device may be advanced toward the stent 100 and used to briefly apply heat to the stent 100, thereby deforming the stent 100 and closing or restricting the aperture 140. If the device is inserted in the lumbar region, the device may be advanced either 1.) from a posterior-lateral region diagonally through the disc annulus central portion 82 to access the end 104; 2.) from a posterior-lateral region and toward the outer surface 78 of the disc wall 74 while not advancing the device through the disc annulus central portion 82 to access the end 106; or 3.) through the anterior region toward the stent 100 to access the end 106. Although, in the lumbar region, it is possible to go through the spinal canal and the spinal fluid, it may be preferable to go around such structures. In the cervical region, the device may be inserted from the anterior portion of the neck for entry. Thus it may be inserted posteriorly through the anterior annulus into the nucleus pulposus.

Another non-limiting example of deforming the stent 100 is to engage the stent 100 with a tool that mechanically deforms either the end 104 or end 106 by crushing or collapsing at least a portion of the stent 100 to restrict the aperture 140.

In some situations, the stent 100 may need to be dislodged. In some implementations, the stent 100 may be dislodged mechanically. In some implementations, the stent 100 may be pushed past the disc annulus and thus out of the disc anteriorly to stop or slow flow of nucleus pulposus 60 out of the disc. In some implementations, a hook or like device may be used to pull the stent 100 entirely into the nucleus pulposus 60 area to stop the flow of nucleus pulposus out of the disc.

In some implementations, the stent 100 may be removed with an additional surgical procedure to access the stent and remove, or by attaching a wire 170 (FIG. 13) to the stent 100 at either the end 104 or the end 106. In some implementations, the wire 170 may have a gripping portion 172 coupled to the end that opposes the end connected to the stent 100. The gripping portion 172 may extend outside the patient, or may be left within the patient in a desired location. In some implementations, the gripping portion may be constructed of a MRI visible or other material to aid in locating the gripping portion 172 when the stent 100 is to be removed. In some implementations, when the stent 100 is to be removed, the gripping portion 172 may be coupled to a device to grasp the wire 170 and pull the stent 100 from the aperture 90. In some implementations, all portions of the stent 100 may not be removed in this procedure, and the portions removed may permit the remainder of the stent 100 to collapse within the aperture 90, thus restricting the aperture 140. In some implementations, after the stent 100 (or portions thereof) are removed from the aperture 90, the stent 100 and wire 90 may be removed from the patient or left inside the patient. In some implementations, the stent 100 may not cause any difficulty if the stent 100 were to be desirably left in the anterior region of the column 20.

In the implementation illustrated, the stent 100 may be implanted by advancing a device through the disc annulus central portion 82, although the stent 100 may be implanted into the wall 74 by accessing the annular wall 74 from the anterior region. One possible reason for advancing the device 120 through the disc annulus central portion 82 prior to forming the aperture 90 is that the disc 46 may be located in the lower portion of the column 20 such that the disc 46 is more easily accessed from a posterior (FIG. 2) region. However, in upper regions of the column 20, the disc wall 74 may be desirably and/or more easily accessed from the anterior region. When the disc 74 is accessed from the anterior region, then the cannula 102 may not be advanced through the disc annulus central portion 82.

Figure 11:
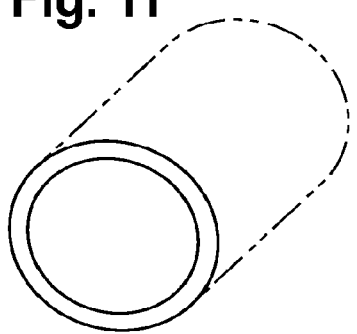
FIGS. 11-13 illustrate exemplary additional implementations of stents.
Figure 12:
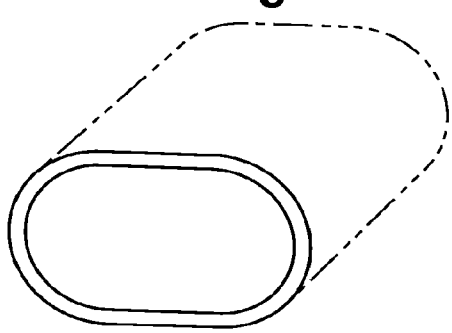
Figure 13:
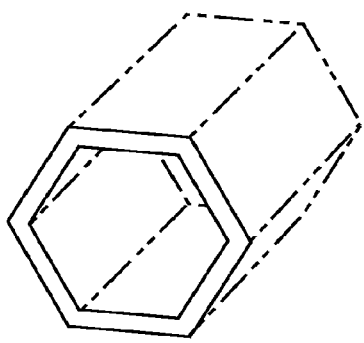

In the implementation illustrated, the stent 100 is helical. However, any other geometries or shapes, such as a woven cylindrical structure, a square or oval structure or other suitable structure may be used. Some other geometries are illustrated in FIGS. 11-13, although other suitable geometries are contemplated. Further, the stent 100 may be constructed of a metal helical core surrounded by a bioabsorbable helical sheathing to permit the stent 100 to bioabsorb, if desired.

In some implementations, the stent 100 does not reinforce the disc or support the vertebrae, but rather is about as deformable as the disc 46 in order to remain within the disc wall 75 as the column 20 is articulated.

Therefore, in some implementations, the diameter of the aperture 140 may be desirably varied based upon the expected viscosity or water content of the nucleus pulposus 60. That is, generally, a patient in the age range of mid 40's may have a nucleus pulposus 60 that is relatively more liquid and an aperture 90 of a desired diameter may be formed to accommodate a stent 100 with a selected stent effective flow area. Additionally, a patient in the age range of mid 70's may have a nucleus pulposus 60 that is relatively less liquid and an aperture 90 of a larger diameter may be formed to accommodate a larger stent 100 with a larger stent effective flow area. In this manner, the stent diameter 140 and stent effective flow area may be varied to accommodate an expected viscosity or liquidity of the nucleus pulposus 60 of the particular patient. Further, the stent 100 may be supplied in a configuration that provides an aperture 140 with a larger stent effective flow area and the stent 100 (at either end 106, end 104, or a central portion) may be deformed to adjust the stent effective flow area as the stent 100 is implanted into the disc wall 74, thereby providing a desired flow rate of the nucleus pulposus 60 for the particular patient.

Although the steps of the method of implanting the stent 100 and restricting the aperture 140 may be listed in an order, the steps may be performed in differing orders or combined such that one operation may perform multiple steps. Furthermore, a step or steps may be initiated before another step or steps are completed, or a step or steps may be initiated and completed after initiation and before completion of (during the performance of) other steps.

A number of implementations have been described. Nevertheless, it will be understood that various modifications may be made without departing from the spirit and scope of the disclosures in this application. As a non-limiting example, in some implementations, the stent 100 may be coated with a chemotherapy material that may prevent or substantially prevent inflammation that may be caused when the nucleus pulposus is extruded from the annulus. As another non-limiting example, the stent 100 may be inserted.

What is claimed is:

1. A method of reducing pressure within a spinal disc comprising:
   forming an aperture within a spinal disc body; and
   permitting at least a portion of the nucleus pulposus to flow from the disc body through the aperture;
   positioning the stent at least partially within the aperture; and estimating a desired amount of time for the aperture to permit the flow of the nucleus pulposus therethrough.

2. The method of claim 1, further comprising at least partially blocking the aperture to limit flow of the nucleus pulposus therethrough.

3. The method of claim 2, wherein at least partially blocking the aperture is performed in a time frame of about 2 weeks to about 8 weeks after forming the aperture.

4. The method of claim 3, wherein at least partially blocking the aperture includes deforming at least a portion of the aperture.

5. The method of claim 1, further comprising implanting the stent within the aperture via a cannula.

6. The method of claim 1, further comprising providing the stent body in a generally helical shape prior to insertion.

7. The method of claim 1, further comprising forming the stent body from a biodegradable material.

8. The method of claim 1, further comprising coating the stent body with a chemotherapy material.

9. The method of claim 1, wherein forming the aperture includes forming the aperture on an anterior or lateral portion of the disc body.

10. The method of claim 1, wherein forming the aperture comprises advancing a device through a disc annulus central portion.

11. The method of claim 1, further comprising using at least one of a burn hole, drill hole, balloon dilation, incision and puncture.

12. A method of reducing pressure within a spinal disc comprising:
    forming an aperture within a spinal disc body;
    permitting at least a portion of the nucleus pulposus to flow from the disc body through the aperture;
    positioning the stent at least partially within the aperture; and
    at least partially blocking the aperture including inserting a plug into the aperture.

13. A method of reducing pressure within a spinal disc comprising:
    forming an aperture within a spinal disc body; and
    permitting at least a portion of the nucleus pulposus to flow from the disc body through the aperture; positioning a stent at least partially within the aperture; and
    at least partially blocking the aperture by accessing the stent from inside a disc annulus central portion.

14. The method of claim 13, further comprising removing the stent.

15. A method of reducing pressure within a spinal disc comprising:
    forming an aperture within a spinal disc body;
    permitting at least a portion of the nucleus pulposus to flow from the disc body through the aperture;
    positioning the stent at least partially within the aperture, and
    at least partially blocking the aperture to limit flow of the nucleus pulposus therethrough.

16. The method of claim 15, wherein at least partially blocking the aperture includes deforming at least a portion of the stent.

17. The method of claim 16, wherein deforming at least a portion of the stent includes applying heat to at least a portion of the stent.

18. The method of claim 15, wherein at least partially blocking the aperture includes collapsing at least a portion of the stent.

19. The method of claim 15, further comprising dislodging the stent.

20. The method of claim 15 further comprising plugging the stent body at least partially within the aperture.

21. The method of claim 15, further comprising removing the stent.

* * * * *